(12) United States Patent
Maguire

(10) Patent No.: US 9,150,539 B2
(45) Date of Patent: Oct. 6, 2015

(54) CRYSTALLINE FORM OF A REVERSE TRANSCRIPTASE INHIBITOR

(71) Applicant: Merck Sharp & Dohme Corp., Rahway, NJ (US)

(72) Inventor: Courtney K. Maguire, Piscataway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/430,657

(22) PCT Filed: Sep. 20, 2013

(86) PCT No.: PCT/US2013/060787
§ 371 (c)(1),
(2) Date: Mar. 24, 2015

(87) PCT Pub. No.: WO2014/052171
PCT Pub. Date: Apr. 3, 2014

(65) Prior Publication Data
US 2015/0232447 A1     Aug. 20, 2015

Related U.S. Application Data

(60) Provisional application No. 61/705,780, filed on Sep. 26, 2012.

(51) Int. Cl.
*C07D 401/06*     (2006.01)

(52) U.S. Cl.
CPC .................................. *C07D 401/06* (2013.01)

(58) Field of Classification Search
CPC ...................................................... C07D 401/06
USPC ....................................................... 546/272.4
See application file for complete search history.

(56) References Cited

U.S. PATENT DOCUMENTS

2005/0222134 A1   10/2005  Busacca et al.
2011/0245296 A1   10/2011  Burch et al.

FOREIGN PATENT DOCUMENTS

WO         2011126969 A1   10/2011

*Primary Examiner* — Patricia L Morris
(74) *Attorney, Agent, or Firm* — Carol S. Quagliato; Laura M. Ginkel

(57) ABSTRACT

The retrovirus designated human immunodeficiency virus (HIV), particularly the strains known as HIV type-1 (HIV-I) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. The invention is directed to a novel crystalline form of the RT inhibitor 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile used in the treatment HIV infection and AIDS.

6 Claims, 9 Drawing Sheets

CRYSTALLINE FORM OF A REVERSE TRANSCRIPTASE INHIBITOR

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz, abacavir, emtricitabine, and tenofovir.

The RT inhibitor 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile and methods for making the same are illustrated in WO 2011/120133 A1, published on Oct. 6, 2011, and US 2011/0245296 A1, published on Oct. 6, 2011, both of which are hereby incorporated by reference in their entirety. The present invention is directed to a novel crystalline form of anhydrous 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile ("Compound A").

SUMMARY OF THE INVENTION

The invention is directed to a novel crystalline form of anhydrous 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile.

BRIEF DESCRIPTION OF THE DRAWINGS

The invention is described in connection with the appended drawings in which.

DETAILED DESCRIPTION OF THE INVENTION

Figure 1:
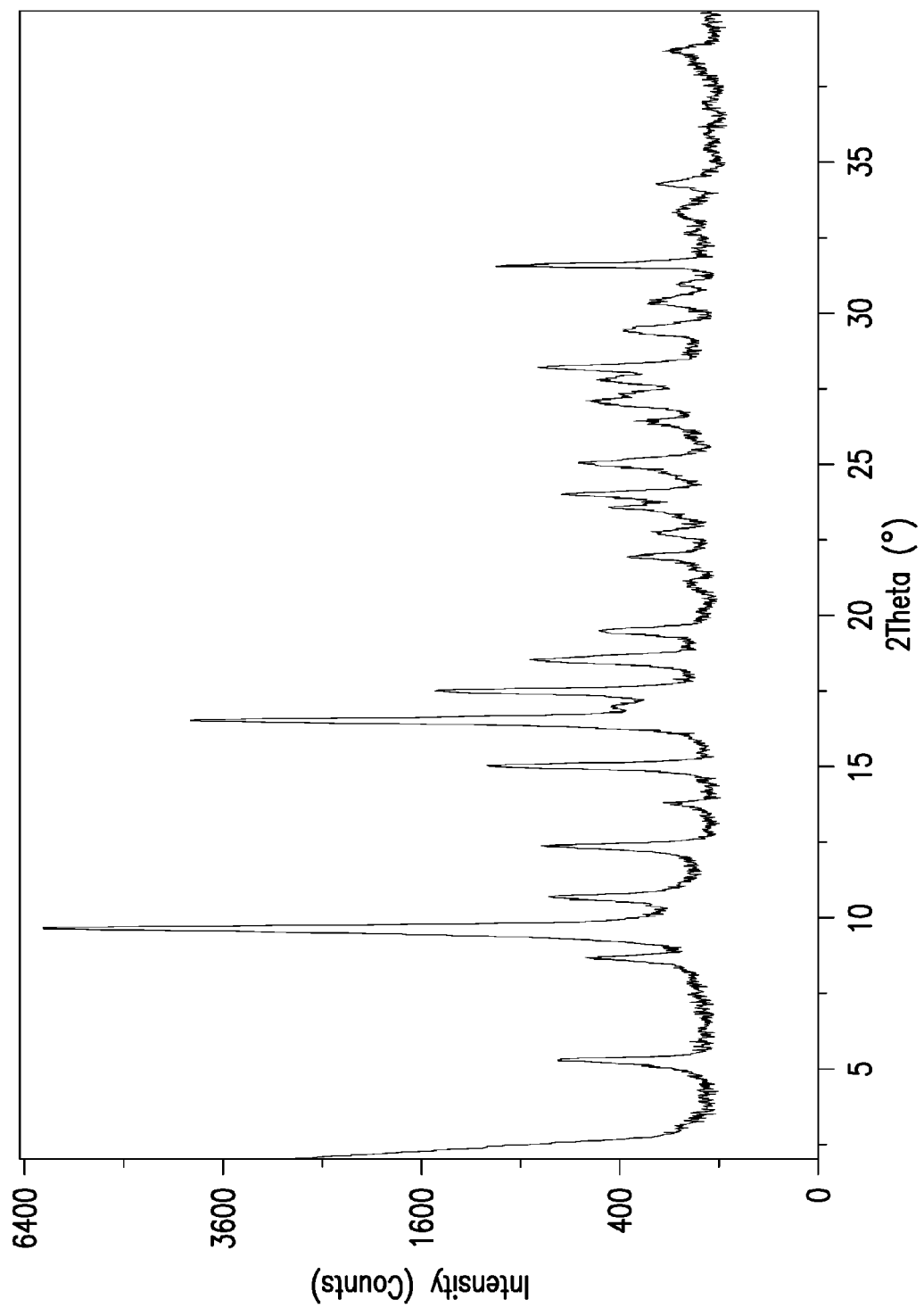
FIG. 1 is the X-ray diffraction pattern (XRPD) of the crystalline anhydrous Form I of Compound A.

"Compound A" as used herein refers to the compound having the chemical name 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile and the following chemical structure.

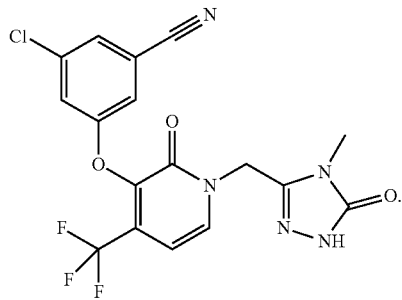 [SMILES: Cn1c(Cn2ccc(C(F)(F)F)c(Oc3cc(Cl)cc(C#N)c3)c2=O)n[nH]c1=O]

Production and the ability of Compound A to inhibit HIV reverse transcriptase is illustrated in WO 2011/120133 A1, published on Oct. 6, 2011, and US 2011/0245296 A1, published on Oct. 6, 2011, both of which are hereby incorporated by reference in their entirety. Compound A is useful for the treatment of human immunodeficiency virus infection is humans. Described herein are crystalline anhydrous forms of Compound A, designated as Form I and Form II, and an amorphous form.

An embodiment of the invention is directed to anhydrous Form II of the compound of Formula A having one or more of the characteristics as defined below. In another embodiment, anhydrous Form II of the compound of Formula A is in substantially pure form. The term "substantially pure" means a particular form substantially free of other forms. In an embodiment, the invention encompasses anhydrous Form II of the compound of Formula A which is at least 95% pure. In another embodiment, the invention encompasses anhydrous Form II of the compound of Formula A which is 90 to 95% pure. In another embodiment, the invention encompasses anhydrous Form II of the compound of Formula A which is 80 to 95% pure. In another embodiment, the invention encompasses anhydrous Form II of the compound of Formula A which is 70 to 95% pure.

Description of Physical Characterization Methods

The crystalline anhydrous Forms I and II and amorphous forms of Compound A were characterized by one or more of X-ray powder diffraction (XRPD), carbon-13 solid state NMR (ssNMR) and Differential Scanning calorimetry (DSC).

X-Ray Powder Diffraction (XRPD)

X-ray powder diffraction studies are widely used to characterize molecular structures, crystallinity, and polymorphism. The X-ray powder diffraction patterns of Forms I, Form II and amorphous form of Compound A were generated on a Philips Analytical X'Pert PRO X-ray Diffraction System with PW3040/60 console. A PW3373/00 ceramic Cu LEF X-ray tube K-Alpha radiation was used as the source. For purposes of d-spacing, the term "about" means±0.1 angstroms.

Solid State NMR

Carbon-13 cross-polarization and magic angle sample spinning (CPMAS) spectra were recorded on a Bruker AV400 400 MHz instrument using a Bruker 4 mm HXY triple resonance CPMAS probe. The carbon-13 spectra were collected utilizing proton/carbon-13 variable-amplitude cross-polarization (VACP) with a contact time of 3 ms, a MAS rate of 13 kHz, and a pulse delay of 64 s. Proton powers of 100 kHz and 83 kHz were used for $\pi/2$ pulses and CP Bruker ramp.100 ramps, respectively. The carbon-13 CP pulse powers were callibrated for maximum signal. SPINAL64 decoupling at 100 kHz was applied during data collection using a it pulse of 4.6 µs. A line broadening of 30 Hz was applied to the carbon-13 spectra before Fourier Transformation and phase correction. Carbon-13 chemical shifts are reported on the TMS scale using the carbonyl carbon of glycine (176.7 ppm.) as a secondary reference. For purposes of solid state NMR, the term "about" means±0.1 ppm.

Differential Scanning Calorimetry (DSC)

DSC data were acquired using a TA Instruments DSC 2910 or equivalent instrumentation. A sample with a weight between 2 and 6 mg is weighed into an open pan. This pan is placed in the sample position in the calorimeter cell. An empty pan is placed in the reference position. The calorimeter cell is closed and a flow of nitrogen is passed through the cell. The heating program is set to heat the sample at a heating rate of 10° C./min to a temperature of approximately 350° C. When the run is completed, the data are analyzed using the DSC analysis program in the system software. The observed endo- and exotherms are integrated between baseline temperature points that are above and below the temperature range over which the endotherm is observed. The data reported are the onset temperature, peak temperature and enthalpy.

Physical Characterization of Compound A Crystalline Anhydrous Form I

X-Ray Powder Diffraction

FIG. 1 shows the characteristic X-ray diffraction pattern of the crystalline anhydrous Form I of Compound A. Characteristic reflections and the corresponding d-spacings for crystalline anhydrous Form I are given in Table 1. Anhydrous Form I of Compound A exhibited characteristic diffraction peaks corresponding to d-spacings of about 9.1, 5.3, and 5.0 angstroms. Anhydrous Form I of Compound A was further characterized by the d-spacings of about 8.3, 7.1, and 3.5 angstroms. Anhydrous Form I of Compound A was even further characterized by the d-spacings of about 4.8 and 3.0 angstroms.

TABLE 1

Characteristic reflections and the corresponding d-spacings for crystalline anhydrous Form I.

| No. | Pos. [°2Th.] | d-spacing [Å] |
|---|---|---|
| 1 | 2.1 | 41.6 |
| 2 | 5.3 | 16.6 |
| 3 | 8.7 | 10.1 |
| 4 | 9.7 | 9.1 |

TABLE 1-continued

Characteristic reflections and the corresponding d-spacings for crystalline anhydrous Form I.

| No. | Pos. [°2Th.] | d-spacing [Å] |
|---|---|---|
| 5 | 10.7 | 8.3 |
| 6 | 12.4 | 7.1 |
| 7 | 15.1 | 5.9 |
| 8 | 16.6 | 5.3 |
| 9 | 17.6 | 5.0 |
| 10 | 18.6 | 4.8 |
| 11 | 19.6 | 4.5 |
| 12 | 21.1 | 4.2 |
| 13 | 22.0 | 4.0 |
| 14 | 22.8 | 3.9 |
| 15 | 23.6 | 3.8 |
| 16 | 24.1 | 3.7 |
| 17 | 25.2 | 3.5 |
| 18 | 27.4 | 3.3 |
| 19 | 29.5 | 3.0 |
| 20 | 30.5 | 2.9 |
| 21 | 31.0 | 2.9 |
| 22 | 34.3 | 2.6 |
| 23 | 38.8 | 2.3 |

Differential Scanning Calorimetry

Figure 2:
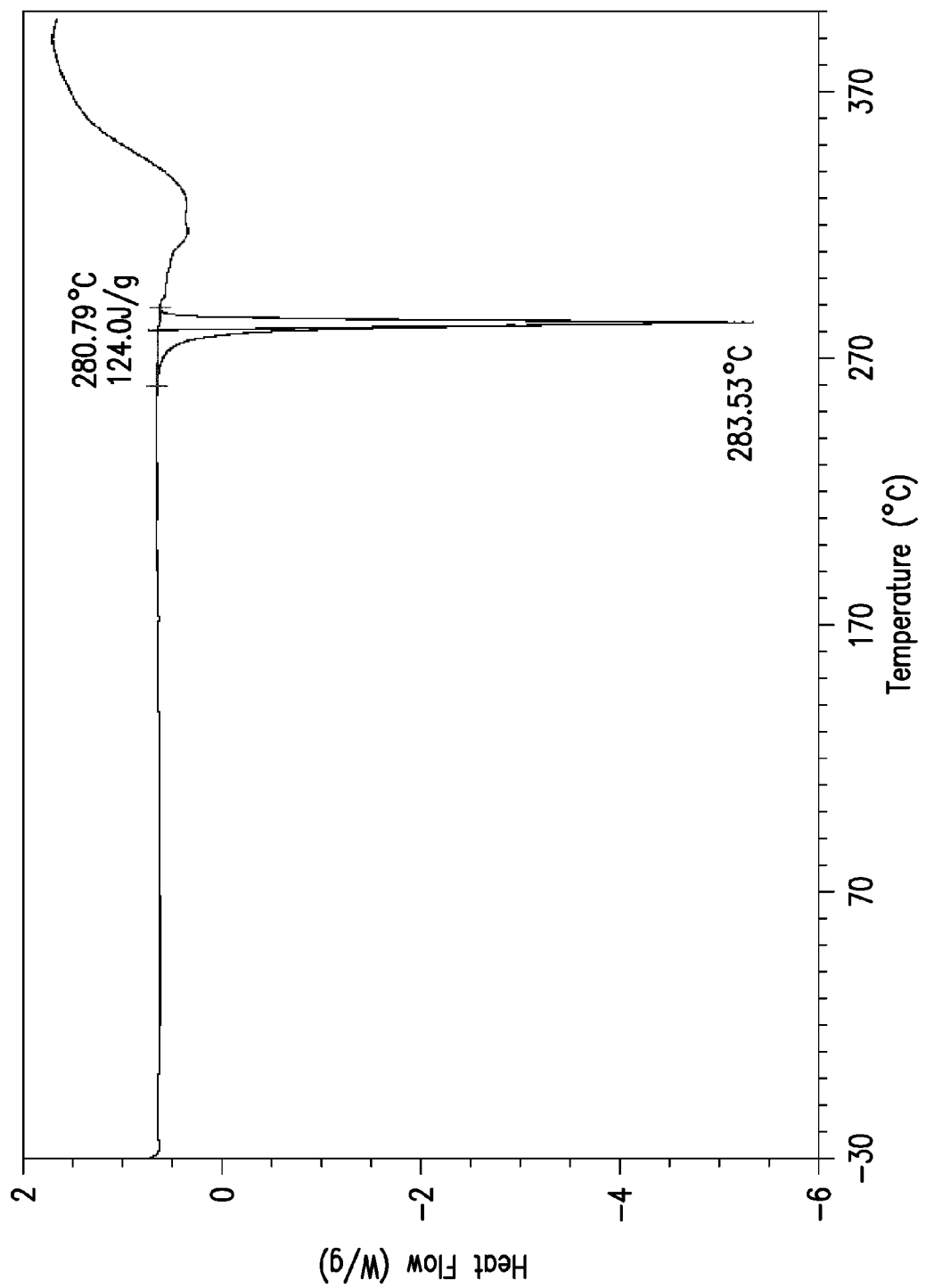
FIG. 2 is the Differential scanning calorimetry (DSC) curve of the crystalline anhydrous Form I of Compound A.

FIG. 2 shows the characteristic differential scanning calorimetry (DSC) curve of the crystalline anhydrous Form I of Compound A. The DSC plot for the sample shows an endotherm with an onset at 280.8° C., a peak maximum at 283.5° C., and an enthalpy change of 124.0 J/g.

Solid State NMR

Figure 3:
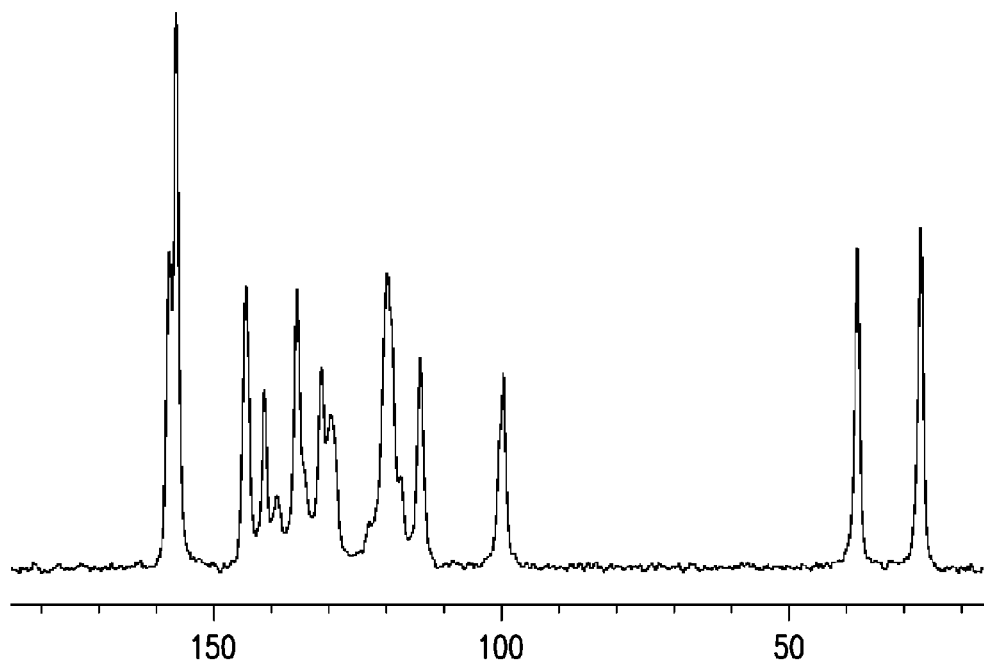
FIG. 3 is the C-13 cross-polarization and magic angle sample spinning (CPMAS) solid state NMR spectrum of the crystalline anhydrous Form I of Compound A.

FIG. 3 shows the carbon-13 CPMAS ssNMR spectrum for the crystalline anhydrous Form I of Compound A. Characteristic peaks are observed at about 27.5, 38.6, 99.8, 114.2, 119.9, 129.7, 131.3, 135.5, 138.9, 141.1, 144.4, 156.4 and 157.6 ppm.

Physical Characterization of Compound A Crystalline Anhydrous Form II

X-Ray Powder Diffraction

Figure 4:
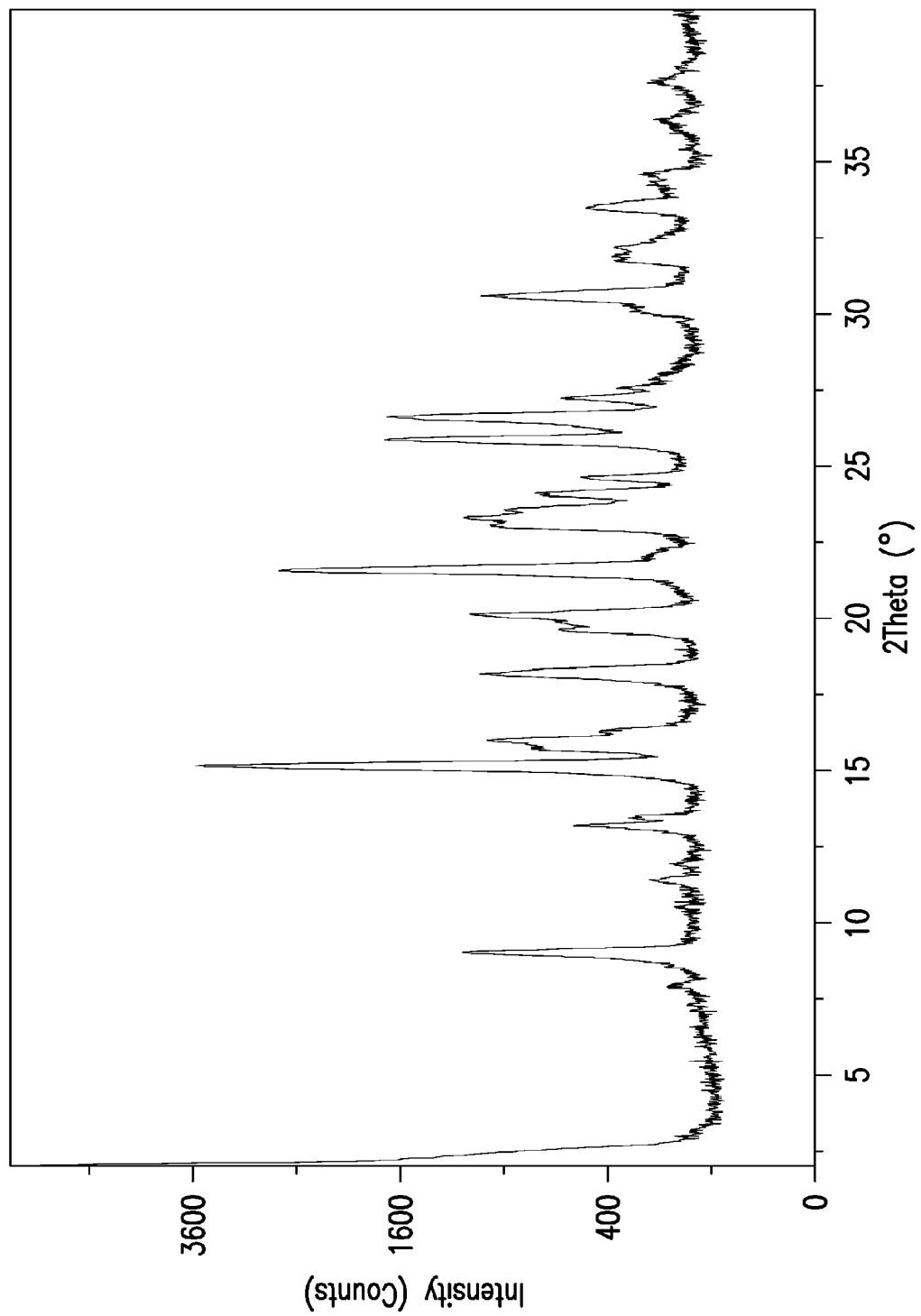
FIG. 4 is the XRPD of the crystalline anhydrous Form II of Compound A.

FIG. 4 shows the characteristic X-ray diffraction pattern of the crystalline anhydrous Form II of Compound A. Characteristic reflections and the corresponding d-spacings for crystalline anhydrous Form II of Compound A are given in Table 2. Anhydrous Form II of Compound A exhibited characteristic diffraction peaks corresponding to d-spacings of about 9.8, 4.9, and 4.1 angstroms. Anhydrous Form II of Compound A was further characterized by the d-spacings of 5.5, 4.4, and 3.8 angstroms. Anhydrous Form II of Compound A was even further characterized by the d-spacings of 7.8, 6.7, and 2.7 angstroms.

An embodiment of the invention encompasses crystalline anhydrous Form II of Compound A having any three or more of the peaks defined in Table 2. Another embodiment of the invention encompasses crystalline anhydrous Form II of Compound A having any six or more of the peaks defined in Table 2. Another embodiment of the invention encompasses crystalline anhydrous Form II of Compound A having all the peaks defined in Table 2.

TABLE 2

Characteristic reflections and the corresponding d-spacings for crystalline anhydrous Form II.

| No. | Pos. [°2Th.] | d-spacing [Å] |
|---|---|---|
| 1 | 2.2 | 40.9 |
| 2 | 5.5 | 16.2 |
| 3 | 9.1 | 9.8 |

TABLE 2-continued

Characteristic reflections and the corresponding
d-spacings for crystalline anhydrous Form II.

| No. | Pos. [°2Th.] | d-spacing [Å] |
|---|---|---|
| 4 | 11.4 | 7.8 |
| 5 | 13.2 | 6.7 |
| 6 | 15.2 | 5.8 |
| 7 | 16.1 | 5.5 |
| 8 | 18.2 | 4.9 |
| 9 | 19.6 | 4.5 |
| 10 | 20.2 | 4.4 |
| 11 | 21.6 | 4.1 |
| 12 | 23.0 | 3.9 |
| 13 | 23.3 | 3.8 |
| 14 | 24.1 | 3.7 |
| 15 | 24.7 | 3.6 |
| 16 | 25.9 | 3.4 |
| 17 | 26.6 | 3.4 |
| 18 | 27.3 | 3.3 |
| 19 | 30.6 | 2.9 |
| 20 | 31.7 | 2.8 |
| 21 | 33.5 | 2.7 |
| 22 | 34.6 | 2.6 |
| 23 | 36.3 | 2.5 |
| 24 | 37.7 | 2.4 |

Differential Scanning Calorimetry

Figure 5:
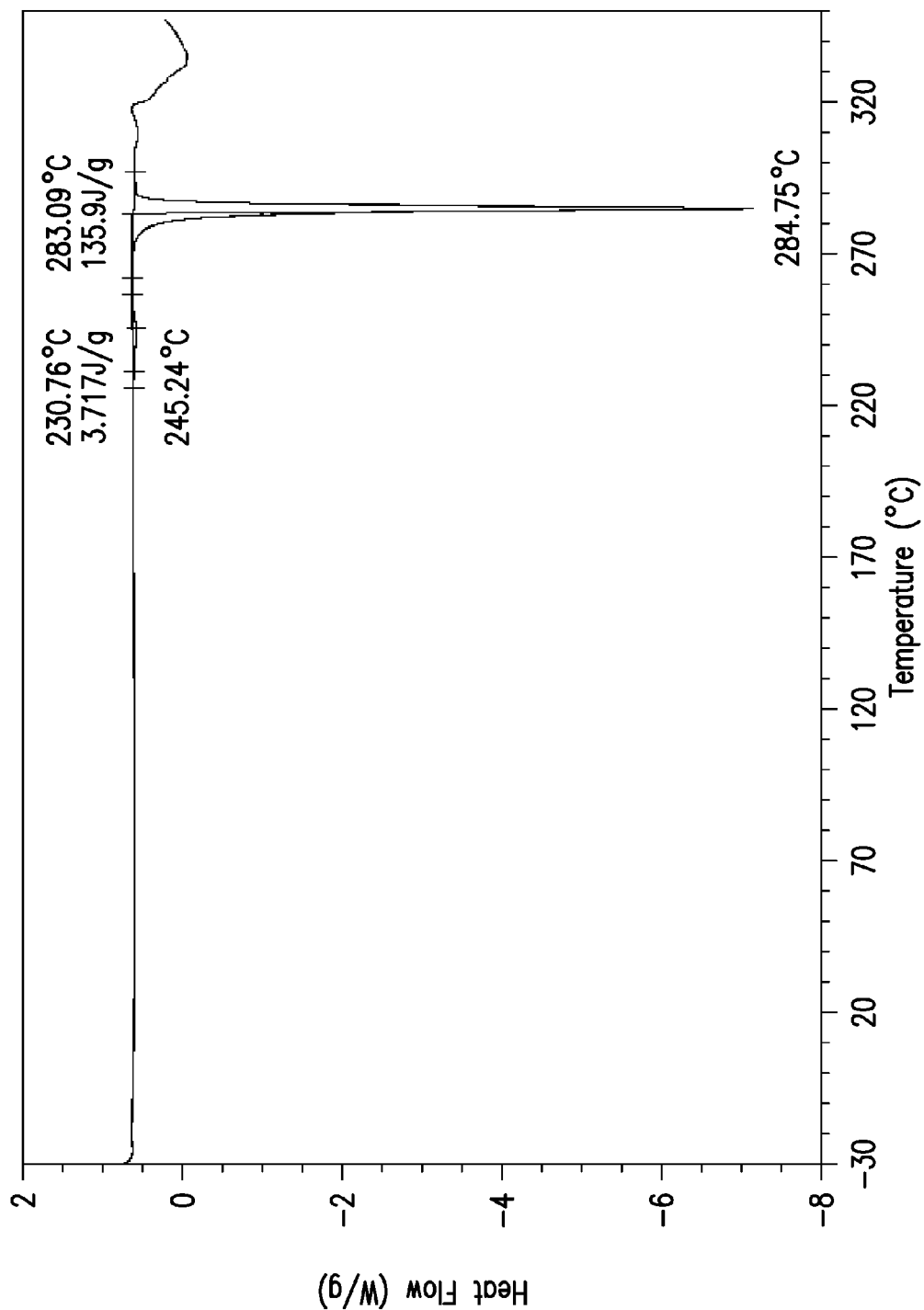
FIG. 5 is the DSC curve of the crystalline anhydrous Form II of Compound A.
Figure 6:
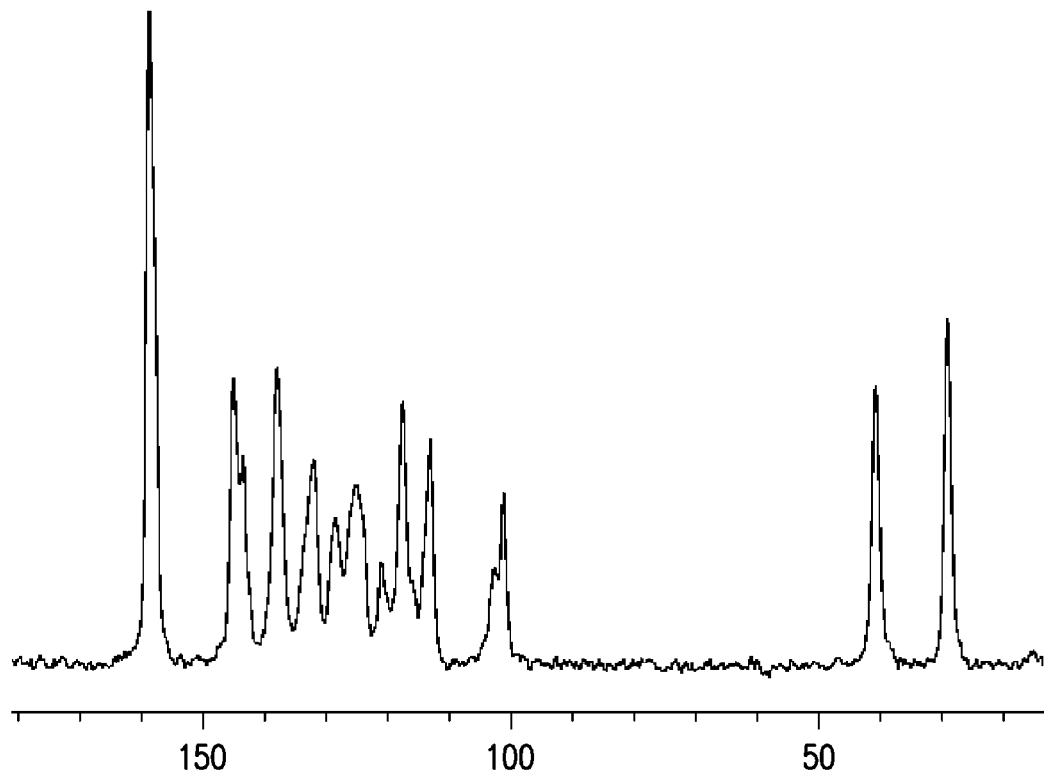
FIG. 6 is the C-13 CPMAS solid state NMR spectrum of the crystalline anhydrous Form II of Compound A.

FIG. 5 shows the characteristic differential scanning calorimetry (DSC) curve of the crystalline anhydrous Form II of Compound A. The DSC curve for crystalline anhydrous Form II of Compound A shows an endotherm with an onset at 230.8° C., a peak maximum at 245.2° C., and an enthalpy change of 3.7 J/g, which is due to polymorphic conversion of anhydrous Form II to anhydrous Form I, and a second melting endotherm with an onset at 283.1° C., a peak maximum at 284.8° C., and an enthalpy change of 135.9 J/g, due to melting of Anhydrous Form I Solid State NMR FIG. 6 shows the carbon-13 CPMAS ssNMR spectrum for the crystalline anhydrous Form II of Compound A. Characteristic peaks are observed at about 29.1, 40.8, 101.1, 102.6, 113.0, 117.5, 121.0, 125.1, 128.4, 132.0, 137.9, 143.5, 145.0 and 158.6 ppm.

Relative Thermodynamic Stability of Crystalline Anhydrous Forms I and II

Competitive slurry experiments were conducted to determine the relative stability of anhydrous Form I and II. It was found that anhydrous Form II is thermodynamically more stable than anhydrous Form I between 5° C. and 70° C. Between 70° C. and 80° C., the relative stability reverses, and at 80° C. anhydrous Form I becomes thermodynamically more stable than anhydrous Form II.

The most thermodynamically stable crystalline form of a drug API is typically desired to avoid transformations during storage and/or shelf life that could alter the in vivo performance and efficacy of a drug.

Physical Characterization of Compound A Amorphous Form

Solid State NMR

Figure 7:
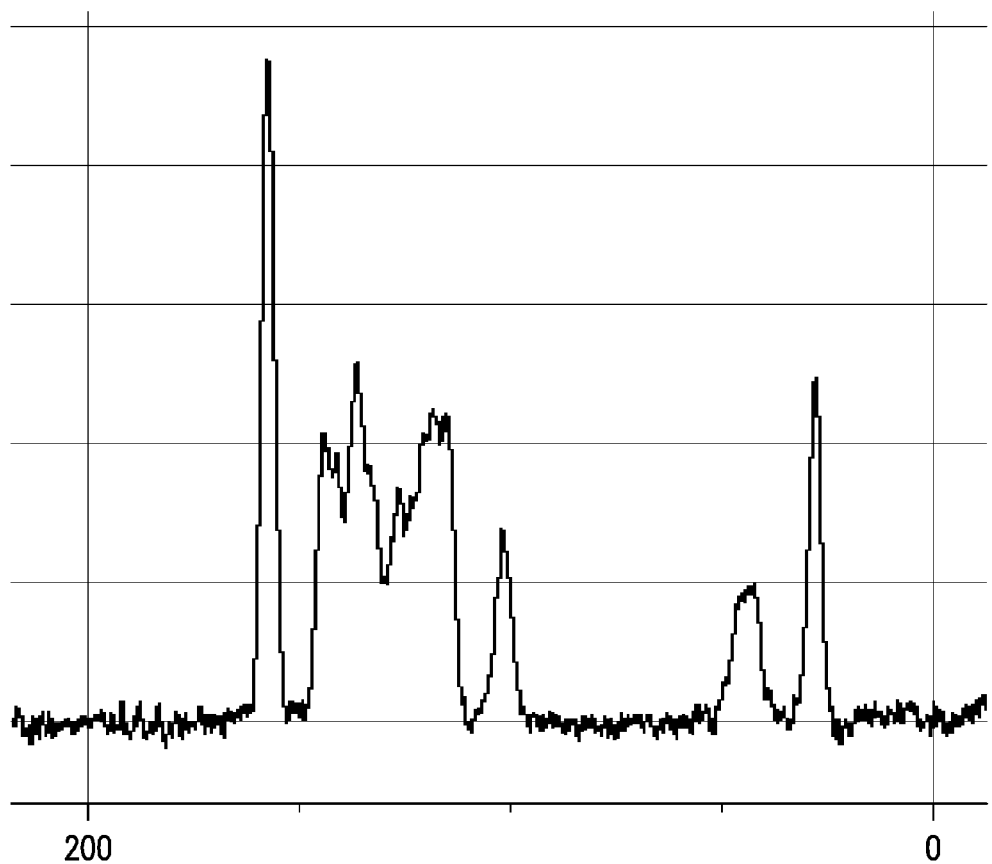
FIG. 7 is the C-13 CPMAS solid state NMR spectrum of the amorphous form of Compound A.

FIG. 7 shows the carbon-13 CPMAS ssNMR spectrum for the Amorphous Form. The spectrum shows broad peaks at about 27.6, 44.0, 101.4, 118.1, 126.1, 134.6, 141.7 and 157.4 ppm, characteristic for the amorphous nature of the material.

Methods of Preparation

Anhydrous Form I ("AHI") and Anhydrous Form II ("AHII") of Compound A are enantiotropic polymorphs with a transition temperature at ~60-70° C. At room temperature, AHII is more thermodynamically stable, but AHI is kinetically favored and the conversion rate from AHI to AHII in solution is very slow under general processing conditions.

Both forms have good solubility (>100 mg/ml at 20-25° C.) in polar aprotic solvents such as dimethyl acetamide (DMAc), N-methyl-pyrrolidinone (NMP), and dimethyl formamide (DMF) at 75 mg/ml. Compound A is soluble to a lesser extent in mixtures of tetrahydrofuran (THF) and water, and the solubility is temperature dependent, making THF/water the ideal candidate for the spray drying process that generates amorphous phase. Compound A is sparingly soluble in other organic solvents such as alcohols and esters, and is poorly soluble in water (<10 ug/ml at 20-25° C.) and hydrocarbons. Therefore, these solvents can act as "antisolvents" to help drive the API out of solution by reducing the solubility.

Consequently, Compound A is readily crystallized in solvent/antisolvent combinations such as DMAc/water, NMP/ethanol (EtOH) and NMP/water. EtOH is preferred due to improved impurity rejection capabilities, while water is preferred for improved productivity and yield due to low API solubility. The crystal form is controlled primarily by choosing the appropriate seed crystals and the batch temperature, and secondarily through control of solubility/supersaturation (via adjusting the solvent composition) and the supersaturation relief rate (via adjusting solvent charge rate or batch cooldown rate). Physical properties such as particle size may be controlled by manipulation of the seed size and seed amount, and also by dry or wet milling processes.

AHI can be generated by a seeded semibatch (forward addition) crystallization process in NMP/EtOH. The API is dissolved in NMP at elevated temperature, cooled to >70° C., and held isothermally while EtOH is charged to reach a suitable seeding composition. AHI solids are charged as seed, and after ageing at >70° C., more EtOH is charged isothermally before the batch is cooled to ambient temperature. For an example of this crystallization refer to Example 5.

AHI can also be generated by a seeded semibatch process in NMP/water, where water is charged to dissolved API in NMP to reach an appropriate seed point. After AHI solids are introduced as seed, more water is charged over time to complete the crystallization.

AHII can be generated in a variety of solvent mixtures by a variety of methods. In the semibatch process, Compound A is dissolved in NMP at <60° C., and EtOH is added to reach an appropriate seed point. AHII seed solids are charged and the batch is aged, followed by further EtOH charge.

AHII can also be generated by semicontinuous crystallization in solvent mixtures such as NMP/EtOH and DMAc/water. In one example, the AHII seed solids are charged to a mixture of DMAc/water to form the seed slurry. Then, API dissolved in DMAc, and water are simultaneously charged to the seed slurry, while maintaining the appropriate solvent composition. More water may be charged to drive Compound A out of solution to improve the yield. In another example of this process, NMP and EtOH replace DMAc and water as the solvent and antisolvent, respectively. For examples of this crystallization refer to Example 5 for DMAc/water.

For particle size control AHII can be milled by (dry) jet mill. Amorphous content generated during dry milling can be converted back to crystalline phase by heat/cool annealing cycle. AHI can also be jet milled.

The AHII crystals also can be wet milled by a media (ball) mill.

Example 1

AHI

Anhydrous Form I of the Compound of Formula A was obtained according to the procedures described in WO 2011/

120133 A1, published on Oct. 6, 2011, and US 2011/0245296 A1, published on Oct. 6, 2011.

Example 2

First Observation of AHII

One mL of 3:1 (v:v) ethanol:toluene was added to 10 mg of Compound A anhydrous Form I. The mixture was stirred at 40° C. for 6 hours. The mixture was then filtered at 55° C. The filtrate solution was evaporated for 3 days at ambient conditions, followed by evaporation under nitrogen gas until all solvent was removed. The isolated solids after evaporation were observed to be birefringent under cross polarized light. The isolated solids were analyzed by X-ray powder diffraction and observed to have a unique XRPD pattern. This new crystal form of the compound of Formula A was designated anhydrous Form II.

Example 3

Process Description for AHI Crystallization 350 g of Compound A solids are dissolved in 1 liter of NMP in the crystallizer vessel, at ca. 350 mg/ml concentration at elevated temperature, ca. 80-95° C. The batch solution is cooled to 75° C., and 0.125 liter of EtOH is charged over 30 minutes to reach a seed point solvent composition 8:1 v:v NMP:EtOH. Charge 3.5-17.5 g (1-5 wt % solids basis) of AHI solids to the crystallizer as seed, and age at 75° C. for 1 hour. About 2.875-3.875 liters of EtOH is charged over 8-12 hours to the vessel to reach solvent composition of between 3:1 v:v and 4:1 v:v EtOH: NMP, while maintaining the batch at 70-75° C. throughout. The batch is then cooled to 20-25° C. over 5 hours, filtered and washed with at least 3.5 liter (10 L/kg) EtOH to remove residual NMP from the solid surface. The wet cake is dried under vacuum at 40-60° C. with nitrogen sweep, and XRD is used to confirm AHI form.

Example 4

Process Description for AHII Crystallization

All operations take place at room temperature, at ca. 20-25° C. 150 grams of Compound A solids are dissolved in 1 liter of DMAc at ca. 150 g/ml concentration to form the Batch Concentrate solution. Separately, DMAc and water are combined at 3:1 v:v ratio to form the heel solution. 0.2 L of the 3:1 v:v DMAc:water solution is charged to the crystallizer vessel, along with 3.75-7.5 grams (2.5-5 wt % solids basis) of Compound A AHII solids as seed crystals, to form the "heel slurry". The Batch Concentrate solution and a separate stream of 0.33 liters of DI water are simultaneously charged to the heel slurry in the vessel slowly (charge time in excess of 12 hrs) to maintain the 3:1 v:v DMAc:water solvent ratio. After the simultaneous charge is complete, another 0.77 liters of DI water are charged over about 5 hours to reach a final batch: solvent ratio of 1:1 v:v DMAc:water. The batch is aged for about 1 hour and then filtered. The wet cake is washed with at least 1.5 liter (10 L/kg) of DI water to remove residual DMAc from the crystal surface, then dried under vacuum at ca. 55° C. with nitrogen sweep. XRD is used to confirm the AHII crystal form.

Example 5

Semicontinuous Crystallization of AHII Form 60 ml of 3:1 v:v DMAc:water solution was prepared and enough Compound A solids were charged to form a thin slurry. After ageing at room temperature overnight, the slurry was filtered to generate a saturated solution with ~7 mg/ml of dissolved Compound A. The 3:1 v:v DMAc:water solution was charged to 500 ml flask and agitated at 250 rpm with an overhead stirrer. 2 g (5 wt %) of Compound A AHII solids were charged to the 3:1 v:v DMAc:water solution and aged at room temperature for 30 minutes to form the heel seed slurry.

40 g of Compound A solids were dissolved in 267 ml of DMAc at room temperature to form the Batch Concentrate. The Batch concentrate was charged to the heel slurry in the vessel simultaneously with a separate 89 ml DI water charge, over 20 hours, at room temperature. The charge rates were controlled to maintain 3:1 v:v DMAc:water ratio throughout the simultaneous charge.

Another 178 ml of DI water was charged to the batch over 5 hours to reach crystallization endpoint composition of 1:1 v:v DMAc:water. After ageing at room temperature and confirming the AHII crystal form by XRD, the batch was filtered and washed with 10 L/kg DI water. The solids were dried at 45° C.—under vacuum with nitrogen sweep.

Figure 8:
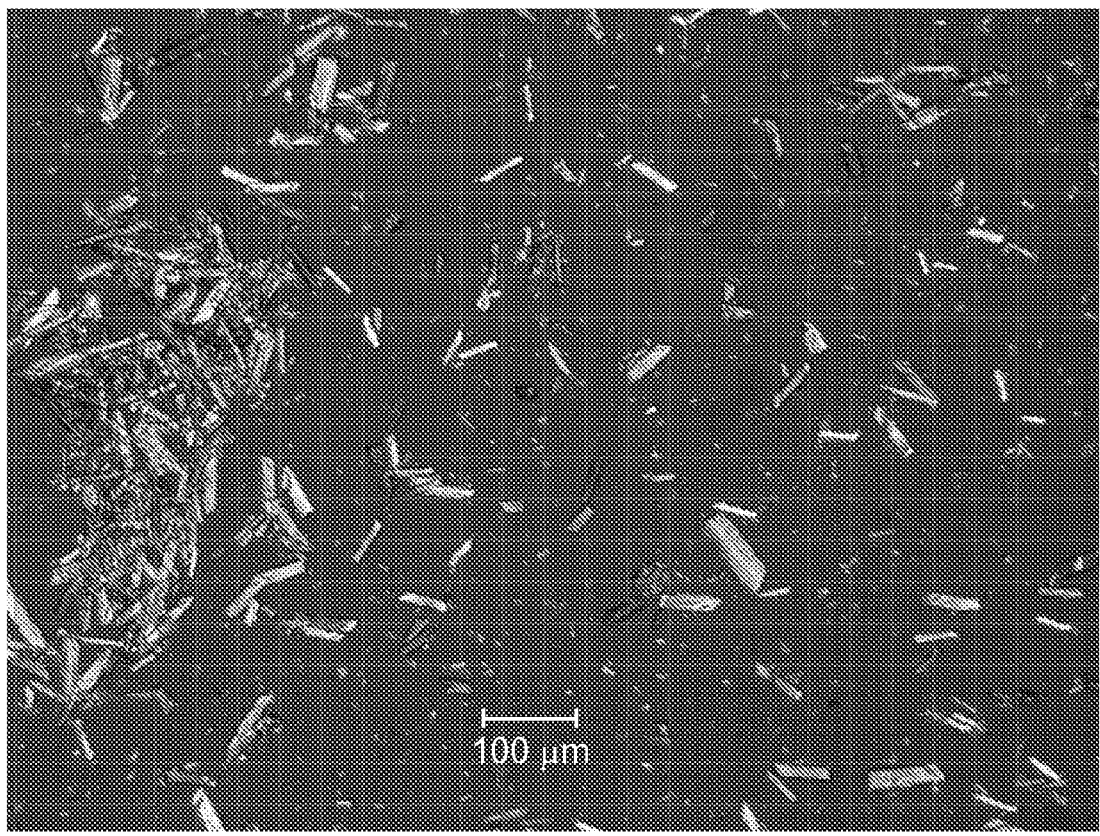
FIG. 8 shows Compound A anhydrous Form II crystals in DMAc/water.

FIG. 8 shows Compound A AHII crystals obtained by the process described in this example.

Example 6

Semibatch Crystallization of AHI Form

Dissolve 4 g of Compound A AHI Crude solids in 13.6 ml NMP (ca. 300 mg/ml concentration) at 70° C. in the 125 ml flask, at 615 rpm agitation rate with overhead stirring. 1.7 ml of EtOH was charged to the batch over 15 minutes, maintaining the temperature at 70° C. The batch solution was seeded with 40 mg (1 wt % solids basis) of Compound A AHI solids, and aged 30 minutes. An additional 56.3 ml EtOH was charged to the batch over 15 hours at 70° C., to reach 4:1 v:v EtOH:NMP endpoint composition. The batch was cooled to 20° C. over 5 hrs and aged at 20° C. for 2 hrs. Solids were filtered and washed with ca. 10 L/kg of EtOH, and was dried under vacuum at 45° C.

Figure 9:
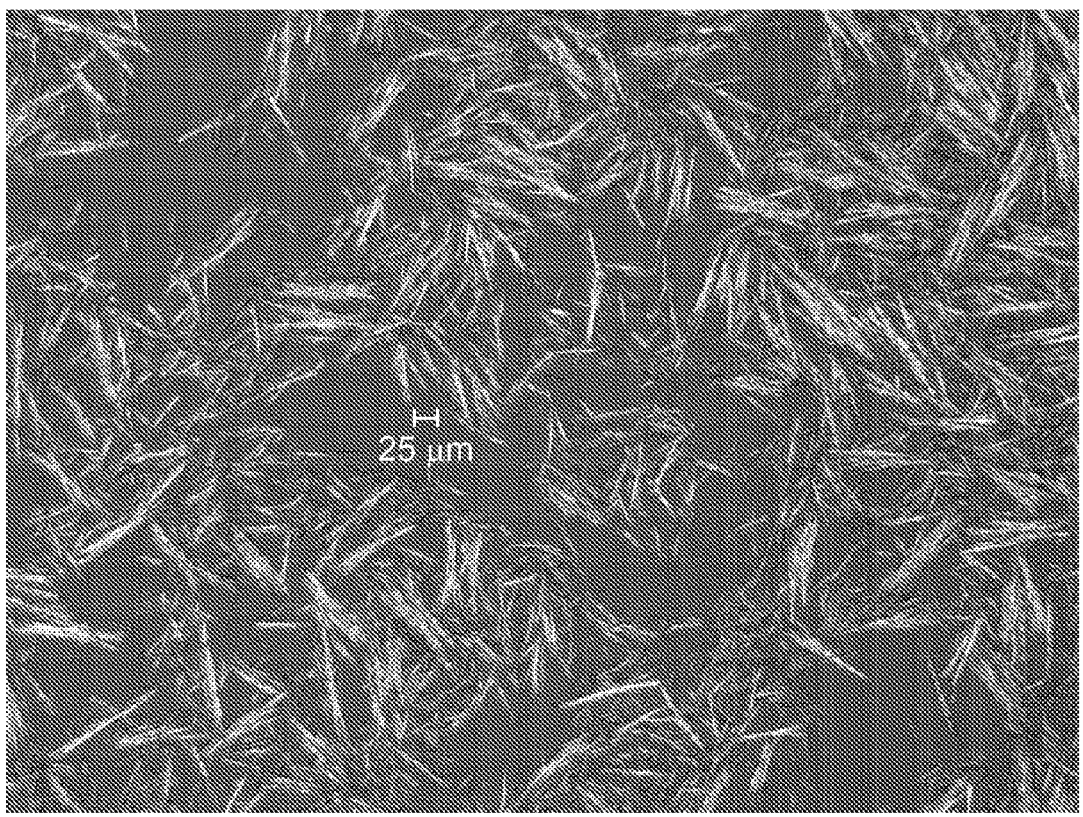
FIG. 9 shows Compound A anhydrous Form I crystals in NMP/EtOH.

FIG. 9 shows Compound A AHI crystals obtained by the procedure described in this example.

Example 7

Semibatch Crystallization of AHII in NMP/EtOH System

Dissolve Compound A crude solids in N-methyl pyrrolidinone (NMP) at ca. 250 mg/ml concentration at 50° C. Charge ethanol (EtOH) to the batch over about 15 minutes to reach seed point of 8:1 v:v NMP:EtOH. Charge 5% AHII seed solids to the batch and age seeded batch for 45 minutes. Charge EtOH over 10 hrs to reach 1:2 v:v NMP:EtOH. Charge EtOH over 5 hrs to each 1:2 v:v NMP:EtOH crystallization end point. Cool batch to 20° C. Filter the solids, wash with EtOH, dry under vacuum at 55° C. with nitrogen sweep.

Example 8

Process Description for Preparation of Amorphous Form 250 mg of Compound A AHII solids were charged to a $ZrO_2$ grinding chamber along with one 20 mm diameter $ZrO_2$ bead. The grinding chamber was agitated for 60 minutes at 15 Hz frequency on a Retsch Type MM301 ball mill. Amorphous was confirmed by ssNMR.

Example 9

Process Description for Preparation of Amorphous Form 300 mg of Compound A AHII solids were charged to a $ZrO_2$ grinding chamber along with one 20 mm diameter $ZrO_2$ bead. The grinding chamber was agitated for 60 minutes at 15 Hz frequency on a Retsch Type MM301 ball mill. Amorphous was confirmed by ssNMR.

Example 10

Process Description for Preparation of Amorphous Form 1 g of Compound A AHI solids were charged to a $ZrO_2$ grinding chamber along with one 20 mm diameter $ZrO_2$ bead. The grinding chamber was agitated for 120 minutes at 15 Hz frequency on a Retsch Type MM301 ball mill. Amorphous was confirmed by ssNMR.

What is claimed is:

1. Crystalline anhydrous Form II of 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile:
   (a) characterized by carbon-13 CPMAS solid state NMR peaks of about: 29.1, 40.8, 101.1, 102.6, 113.0, 117.5, 121.0, 125.1, 128.4, 132.0, 137.9, 143.5, 145.0 and 158.6 ppm; or
   (b) characterized by x-ray powder diffraction, Cu K alpha, peaks corresponding to d-spacings of about: 9.8, 4.9 and 4.1 angstroms; or
   (c) having the following endotherms as determined by DSC:
      (1) an endotherm associated with a polymorphic transition of Compound A crystalline anhydrous Form II into anhydrous Form I with an extrapolated onset temperature in the range of about 130 to about 260° C., a peak temperature in the range of about 245 to about 265° C. and an enthalpy change in the range of about 4 to about 8 J/g; and
      (2) an endotherm with an extrapolated onset melting temperature in the range of about 283 to about 284° C., a peak melting temperature in the range of about 285 to about 287° C. and an enthalpy change in the range of about 127 to about 137 J/g.

2. Crystalline anhydrous Form II of 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile in accordance with claim 1 characterized by x-ray powder diffraction, Cu K alpha, peaks corresponding to d-spacings of about: 9.8, 4.9 and 4.1 angstroms, which is further characterized by x-ray powder diffraction, Cu K alpha, peaks corresponding to d-spacings of about: 5.5, 4.4, and 3.8 angstroms.

3. Crystalline anhydrous Form II of 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile in accordance with claim 2 characterized by x-ray powder diffraction, Cu K alpha, peaks corresponding to d-spacings of about: 9.8, 5.5, 4.9, 4.4, 4.1 and 3.8 angstroms, which is further characterized by x-ray powder diffraction, Cu K alpha, peaks corresponding to d-spacings of about: 7.8, 6.7, and 2.7 angstroms.

4. Crystalline anhydrous Form II of 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile according to claim 1 in substantially pure form.

5. Crystalline anhydrous Form II of 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile according to claim 2 in substantially pure form.

6. Crystalline anhydrous Form II of 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile according to claim 3 in substantially pure form.

* * * * *